United States Patent
Williams et al.

(10) Patent No.: US 10,092,667 B2
(45) Date of Patent: Oct. 9, 2018

(54) HIGH EFFICIENCY POLYMERIC STERILANT CONTAINER ASSEMBLY

(71) Applicant: Brighton Development, LLC, Cary, NC (US)

(72) Inventors: Joel Lawson Williams, Cary, NC (US); Lois A. Jones, Cary, NC (US); Paul M. Vernon, Jr., Chapel Hill, NC (US)

(73) Assignee: Brighton Development, LLC, Cary, NC (US)

( * ) Notice: Subject to any disclaimer, the term of this patent is extended or adjusted under 35 U.S.C. 154(b) by 518 days.

(21) Appl. No.: 14/074,058

(22) Filed: Nov. 7, 2013

(65) Prior Publication Data

US 2014/0056761 A1 Feb. 27, 2014
US 2018/0071419 A9 Mar. 15, 2018

Related U.S. Application Data

(63) Continuation-in-part of application No. 13/372,883, filed on Feb. 14, 2012, now abandoned, which is a continuation-in-part of application No. 12/881,273, filed on Sep. 14, 2010, now abandoned.

(60) Provisional application No. 61/276,944, filed on Sep. 18, 2009.

(51) Int. Cl.
*A61L 2/20* (2006.01)
*B65B 55/02* (2006.01)
*A61L 2/08* (2006.01)
*B65D 33/25* (2006.01)

(52) U.S. Cl.
CPC ............... *A61L 2/204* (2013.01); *A61L 2/081* (2013.01); *B65B 55/02* (2013.01); *B65D 33/2508* (2013.01); *A61L 2202/18* (2013.01); *A61L 2202/181* (2013.01); *A61L 2202/24* (2013.01)

(58) Field of Classification Search
CPC ........................................................ A61L 2/204
See application file for complete search history.

(56) References Cited

U.S. PATENT DOCUMENTS

| | | | |
|---|---|---|---|
| 3,027,352 A | 3/1962 | Walling et al. | |
| 3,658,749 A | 4/1972 | Gordon | |
| 4,050,576 A | 9/1977 | Williams et al. | |
| 5,476,616 A | 12/1995 | Schwarz | |
| 5,594,955 A * | 1/1997 | Sommers | A41D 13/1227 2/114 |
| 6,258,884 B1 * | 7/2001 | Mulholland | C08K 3/22 524/366 |
| 6,818,294 B2 | 11/2004 | Kikutani et al. | |
| RE39,182 E | 7/2006 | Muck et al. | |
| 7,410,696 B2 | 8/2008 | Zierer et al. | |

(Continued)

OTHER PUBLICATIONS

Ron (Rongguo) Zhao, Biax Fiberfilm Corporation, Melt Blowing Polyoxymethlene Copolymer, INJ Summer 2005.

(Continued)

*Primary Examiner* — Donald R Spamer
(74) *Attorney, Agent, or Firm* — James G. Passé; Passé Intellectual Property, LLC

(57) ABSTRACT

The present invention relates to a method for sterilizing an article inside a sealed container by placing a polyoxymethylene melt formable co-polymer fiber that has been irradiated between about 1 and 200 kGy and then heated at from about 20° C. to about 90° C. for a selected period of time.

13 Claims, 1 Drawing Sheet

(56) References Cited

U.S. PATENT DOCUMENTS

2005/0104043 A1\* 5/2005 Lucht .................. G01N 31/229
 252/408.1
2005/0288438 A1 12/2005 Nandi
2006/0009616 A1 1/2006 Muck

OTHER PUBLICATIONS

Celanese, News Releases, Ticona Introduces First Acetal for Meltdown Nonwovens, Jul. 30, 2002.
Ticona Celcon FG40U01 Acetal Copolymer, Nov. 22, 2009.
Ticona Celcon FG40U01 Acetal Copolymer, MatWeb (Material Property Data), Nov. 22, 2009.
"Spinning (polymers)." www.Wikipedia.org. Feb. 10, 2016. https://en.wikipedia.org/wiki/Spinning_(polymers). Accessed Dec. 20, 2016.
Hegde, Raghavendra R., M.G. Kamath, and Atul Dahiya. "Polymer Crystallinity." The University of Tennessee of Knoxville, Tickle College of Engineering. www.engr.utk.edu/mse/Textiles/PolymerCrystallinity.htm.

\* cited by examiner

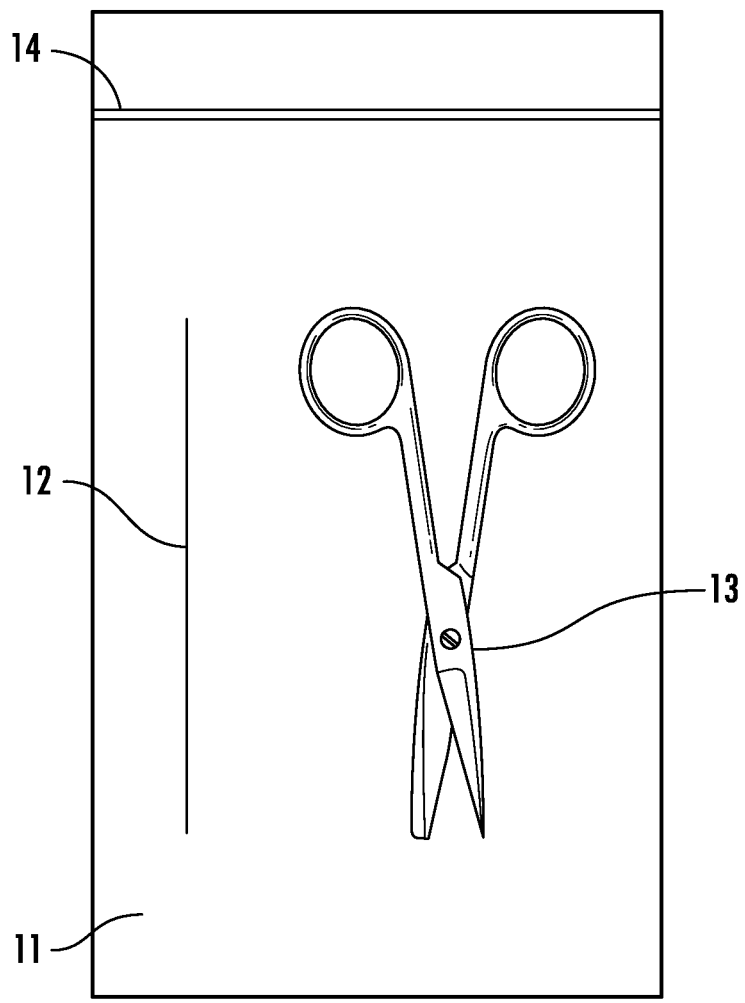

HIGH EFFICIENCY POLYMERIC STERILANT CONTAINER ASSEMBLY

This application is a continuation-in-part of U.S. non-provisional application Ser. No. 13/372,883 filed on Feb. 14, 2012 which is a continuation-in-part of U.S. non-provisional application Ser. No. 12/881,273 filed on Sep. 14, 2010 which claims priority to provisional application No. 61/276,944 filed on Sep. 18, 2009. All applications are incorporated herein in their entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to sterilized packages and containers. In particular, the present invention relates to sterilized packaging containing a highly efficient formaldehyde releasing composition.

Description of Related Art

There is a wide array of medical devices that must be sterilized prior to their use. In the medical field it is common to have articles that can be re-sterilized or disposable articles that are only used one time but are provided to the user already sterilized. The art uses a wide variety of methods to sterilize or re-sterilize medical articles including, ethylene oxide, formaldehyde, low temperature steam-formaldehyde, gamma/e-beam irradiation, steam autoclave, dry heat, and the like.

While gaseous sterilization is very effective, the handling and long periods of time needed to diffuse and remove the sterilant gas from the chamber containing large pallets of heavy cardboard boxes/packages is a problem. Because of the long contact times and purge cycles required for gaseous sterilization, most gaseous sterilizations take place mainly in industrial settings where the requirement for expensive equipment is more cost effective and careful control can take place during the sterilization cycle by someone experienced in the sterilization process. Also, high energy irradiation methods require expensive radiation facilities and certified personnel skilled in the use of radiation isotopes for the purpose of sterilization of medical products. Plastic components of medical products are often embrittled or damaged by the destructive nature of the irradiation process. In the non-industrial setting, such as a hospital or physician's office, historically one of the most widely used methods for sterilization is the use of high temperature steam autoclaves. Unfortunately, the temperature of an autoclave is not conducive for use with many of today's plastics or other heat sensitive medical products which are commonplace in the medical environment of today. Accordingly, many medical offices throw away reusable medical devices because there are currently no techniques that are suitable for the non-industrial setting that are both cost effective and easy to use in small medical facilities.

Some twenty-five years ago an attempt to solve the problem was made in U.S. Pat. No. 4,050,576 to Williams et al. In that patent a sterilant package included a relatively thick piece of poly acetal (which contains oxymethylene groups and stabilizing groups) which had been irradiated to effect chain cleavage of the polymer without depolymerization. The package, upon subsequent heating, caused the poly acetal to slightly depolymerize which caused a release of trace amounts of formaldehyde gas. Unfortunately, the irradiation doses required to achieve sufficient gas release for sterilization using this method were so high that the insert became very brittle and difficult to manage as indicated by low film breaking angles in embrittlement tests.

During the prior art timeframe, thermoplastic polyoxymethylenes were only commercially available as extremely viscous melts (low melt flow rates between 0.3 to 5.0 g/10 min as determined by ASTM D1238E) that limited the thermoformability into simple geometries, such as films, slabs, and rods, which required prolonged crystallization times that caused even further embrittlement and degradation of the material. Relatively thin fibers are impossible to form with these low melt flow rate polymers since spin blown fibers require higher melt flows. Severe plastic embrittlement caused by the combination of thicker part limitations and higher irradiation doses required to achieve sufficient gas release resulted in the prior art never being adopted commercially.

BRIEF SUMMARY OF THE INVENTION

The present invention relates to the discovery that if a low melt viscosity and melt formable (such as by melt blowing) polyoxymethylene or copolymer of polyoxymethylene is formed into a relatively thin fiber with a sufficient high surface to mass ratio and irradiated, it can be included in a package for purposes of sterilization of the contents of the container by low heat release of formaldehyde without becoming too brittle yet still releasing sufficient formaldehyde to sterilize the article. The thin fiber is achieved by utilizing a polyoxymethylene or a co-polymer thereby having a melt flow rate of between about 20-1200 g/10 minutes at 230° C. as determined by ASTM D1238E.

Accordingly, one embodiment of the present invention relates to a container of a selected volume on the inside, suitable for low heat sterilizing a selected article positioned in the inside of the container comprising a container insert on the inside of the container comprising a fiber of a diameter 0.5 mm or less of polyoxymethylene or co-polymer of polyoxymethylene having a melt flow rate of between about 20-1200 g/10 minutes at 230° C. that has been irradiated sufficient to cause chain cleavage without depolymerization or brittleness of the insert such that formaldehyde is released upon subsequent application of low heat to the insert by any manner.

In yet another embodiment of the present invention, there is a process for producing a container of a selected volume on the inside suitable for low heat sterilizing a selected article positioned on the inside of the container comprising positioning in the inside of the container, a fiber having a diameter of 0.5 mm or less comprising a polyoxymethylene or co-polymer having a melt flow rate of between about 20-1200 g/10 minutes at 230° C. and has been irradiated sufficient to cause chain cleavage without depolymerization or brittleness such that formaldehyde is released upon subsequent application of low heat to the insert.

In yet another embodiment of the present invention there is a method of sterilizing an article at low heat in a container of a selected volume on the inside comprising:
  a) positioning the article in the container;
  b) positioning a fiber in the container which comprises a fiber of a diameter of 0.5 mm or less of polyoxymethylene or polyoxymethylene co-polymer having a melt flow rate of between about 20-1200 g/10 minutes at 230° C. that has been irradiated sufficient to cause chain cleavage without depolymerization or brittleness such that formaldehyde is released upon subsequent heating of the insert; and c) heating the fiber to a temperature of about 20° C. to about 90° C. for a time sufficient to release formaldehyde and sterilize the article.

BRIEF DESCRIPTION OF THE DRAWING

FIG. 1 is a medical device in a container with the polymer insert of the present invention.

DETAILED DESCRIPTION OF THE INVENTION

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

DEFINITIONS

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The terms "about" and "essentially" mean ±10 percent.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

The term Melt Flow Rate, as used herein, is defined as the amount of polymer flowing through a hole in g/10 minutes at 230° C. as determined by ASTM D1238E, incorporated herein by reference.

As used herein, the term "container" refers to any package, bag, or the like in which a desired item for sterilization can be enclosed and sealed and having a selected volume on the inside. The container must be capable of withstanding the low heat of the present invention and be essentially impermeable to formaldehyde to prevent its leakage during the sterilization process. In one embodiment the humidity on the inside of the container is about 5-100 percent relative humidity. In one embodiment, the containers are plastic bags made of polyethylene, polypropylene, Saran, aluminum foil or foil coated plastic, and the like. In one embodiment, they are essentially flat bags of the shape and style of food sandwich bags with an appropriate closure (sandwich zip lock). The flat bags will have a selected length and width with an area defined by the product of the length times the width. The bags can be sealed, for example, by an adhesive seal, zipper lock seal, or other methods for sealing the bag. In another embodiment, the article is placed in the bag and the bag heat sealed shut, thus making the bag a one-time disposable bag since the bag must be torn, cut open, or the like to obtain the enclosed sterilized item. In still another embodiment, a combination of zip lock and heat seals are used as tamper-proof seal configurations. In still another embodiment, a chevron seal is provided at the opposite end of the bag to maintain sterility when opening in a sterile field, such as an operating room. The container of the present invention can be any size necessary to contain the item to be sterilized. Accordingly, most any size container can be utilized, but for efficiency sake, the bag would be the minimum size that the article to be sterilized would fit inside the closed portion of the container. For example, a flat, polymeric bag for sterilizing a scalpel would only need to be 4 or 5 inches long and 3 or 4 inches wide while surgical instruments might need to be several feet long.

As used herein "low heat" refers to the ability to apply heat to the insert in the range of about 20° C. to about 90° C. The heat can be applied by any convenient means, such as a gas or electric oven, electric heating wires, heat lamp, chemical reaction, sunlight, or the like. The container could be heated in order to heat the insert in one embodiment. Other embodiments of heating include heating the insert prior to placement in the container incorporating a heating device (e.g. heating wires) inside the insert, internal, or external heating packs (wire heaters or hand warmers). In another embodiment, the insert can be accessed through the container (e.g. a tube that extends through the container wall that can contain a heating element). The exact heat will vary but will depend on the size of the article and the time at the particular heat. In view of the present disclosure, one could easily match the exact heat temperature and time to obtain a sufficient time for heating to release formaldehyde. In one embodiment, the time period of heating is from about 5 minutes to 600 minutes and in another embodiment it is about an hour. In one embodiment the heating could be at room temperature and could be sustained over an extended period of time (days to weeks).

The "selected article" as used herein, is the article that one wishes to sterilize. Since the maximum heat is in the ranges noted above, the article can be made of plastic or other materials that normally would not handle higher heats. Once again, if an article would not survive say, 90° C., the article can be heated at a lower temperature for a longer time and achieve the same result of sterilization though a longer time would be necessary.

As used herein, a "polyoxymethylene (POM)" or "co-polymer of polyoxymethylene" are any polymers which can be melt blown or otherwise melt formable into thin fibers. The fibers will have a diameter of less than about 0.5 mm and in one embodiment less than about 0.1 mm diameter. The POM polymeric materials of the present invention have a very high melt flow rate and consequently are very fluid in the molten state, unlike historical POM's that were extremely viscous in the melt. The high melt flow rate POM's as defined herein are necessary in order to form the high surface area thin fibers without severe thermal degradation of the POM as found historically with low melt flow rate POM's. High melt flow rate polymers are generally used in industry for forming high surface area fibers or melt processing and forming into non-woven fabric or mat type articles. Thermal flow rate of the present invention is tested by ASTM D1238E. The polymer, in order to be spun into fibers of the desired diameter have a melt flow rate of 20-1200 g/10 minutes at 230° C. and another embodiment at about 40-1200 g/10 minutes at 230° C. and 20-500 g/10 minutes at 230° C. Generally, the radiation dosage to accomplish the proper chain cleavage without depolymerization or brittleness, such that formaldehyde is released upon subsequent heating of the insert, is from about 1 to about 200 kGy. In one embodiment the insert is irradiated from about 35 to about 70 kGy.

As used herein a "fiber" is a piece of high melt flow POM melt formed copolymer that has been irradiated sufficiently to cause chain cleavage without depolymerization or brittleness, but sufficiently that formaldehyde is released upon the subsequent low heat sterilizing of the insert for a select period of time. Fiber (with a high surface area) can be formed into a non-woven mat. The fiber needs to be of a sufficient weight and surface area that upon low heat application the container the insert will release sufficient formaldehyde to reach a concentration of at least 0.1 mg/L in the container volume inside. In one embodiment it is of at least 0.3 mg/L formaldehyde. This can be determined by one skilled in the art. The fiber can be a loose piece inside the container, or in other embodiments, it can be attached to or part of the inside surface of the container, for example, by layering the POM co-polymer fiber on the inside of the container especially where the container is a polymeric bag. In some embodiments, the POM co-polymer can be mixed with other polymers or substances to create a multi-component insert for particular additional purposes. In one embodiment, a thermochromic material is added to the POM co-polymer so that when it is heated it will change color at the end of the sterilization heating. The fiber is placed in the container prior to the heating or at the time of heating, as necessary or desired.

In general, the process of sterilizing an article at low heat in a container comprises placing the irradiated fiber and article to be sterilized (in any order) inside the container. The insert is heated to a temperature of about 25° C. to about 90° C. for a time sufficient to release formaldehyde from the container insert and sterilize the article either before placing in the container or afterwards. The container is sealed after fiber placement therein. The package can then be opened and if resealable, reused. The article is then sterilized and ready for the desired sterilized use.

Now referring to the drawing. FIG. 1 is an embodiment of the present invention. There is shown a container 11 suitable for low heat sterilizing. Inside container 11 is a high surface area fiber 12. Also, in container 11 is an article to be sterilized, a surgical tool 13. In this embodiment the container 11 is a zip lock 14 closable container made from a clear polyester material.

EXAMPLE 1

A 10 mil thick sample of POM dense film and an equivalent weight of fiber melt blown POM of the present invention were gamma irradiated to a nominal dose of 70 kGy followed by heating both samples at 70° C. for a period of 60 minutes in a convection oven. The thick film yielded a 0.18% formaldehyde release while the melt blown sample of the present invention yielded a 2.12% release of formaldehyde which is over a ten-fold increase compared to the thick film. In separate experiments, the same level of sterility could be achieved with one-tenth the weight of melt blown material compared to thick film.

Comparative embrittlement bending tests indicated that the thick film failed at a 21 degree bending angle while the melt blown sample could undergo a full 180 degree bend without failure.

EXAMPLE 2

A 10 mil thick sample of POM film and an equivalent weight fiber of melt blown POM of the present invention were both gamma irradiated to a nominal dose of 30 kGy followed by heating both samples at 70° C. for a period of 60 minutes in a convection oven. The film yielded 0.6 mg of formaldehyde while the melt blown sample of the present invention yielded 3.1 mg of formaldehyde or over five-fold more sterilant for equal sample comparison. In separate experiments, the same level of sterility could be achieved with one-fifth the weight of melt blown material compared to thick film.

Comparative embrittlement bending tests indicated that the thick film failed at a 20 degree bending angle while the melt blown sample could undergo a full 180 degree bend without failure.

EXAMPLE 3 TO EXAMPLE 11

Three melt blown samples of high melt flow rate POM (Melt Flow Rate of 40 g/10 minutes at 230° C. as determined by ASTM D1238E) were prepared on a melt-blown processing line at the University of Tennessee with average weights per square meter (GSM) of 100, 150, and 200 GSM. Fibers were formed into a mat configuration. All melt blown mats had average fiber diameters of 10 microns. Stock rolls of the melt blown mats were irradiated to 20, 35, and 50 kGy in a cobalt-60 gamma facility. Following irradiation, 4"×6" samples of each weight melt blown mat were placed into separate 5"×8" zip-lock bags along with a strip of a biological indicator inoculated with either $10^5$ *Geobacillus Stearothermophilus* or $10^6$ *Bacillus Atrophoeous*. All samples after heating to 70° C. for 15 minutes were found to be sterile as shown below:

| Example | GSM | Dose (kGy) | G. Stearothermophilus | B. Atrophoeous |
| --- | --- | --- | --- | --- |
| 3 | 100 | 20 | Sterile | Sterile |
| 4 | 100 | 35 | Sterile | Sterile |

-continued

| Example | GSM | Dose (kGy) | G. Stearothermophilus | B. Atrophoeous |
|---------|-----|------------|----------------------|----------------|
| 5 | 100 | 50 | Sterile | Sterile |
| 6 | 150 | 20 | Sterile | Sterile |
| 7 | 150 | 35 | Sterile | Sterile |
| 8 | 150 | 50 | Sterile | Sterile |
| 9 | 200 | 20 | Sterile | Sterile |
| 10 | 200 | 35 | Sterile | Sterile |
| 11 | 200 | 50 | Sterile | Sterile |

Even the lowest weight 100 GSM mat yielded sufficient sterilant to render the contents of the bag sterile even at the lowest dose of 20 kGy.

TABLE 1

Antimicrobial effectiveness of the test material with indirect contact with microbial contamination.

| Test Sample | S. aureus | P. aeruginosa |
|-------------|-----------|---------------|
| 1) Inoculated lens on antimicrobial material | S | S |
| 2) Inoculated lens on material with multipurpose lens solution | S | S |
| 3) Inoculated lens on material with sterile buffer solution | S | S |
| 4) Negative control 1 | S | S |
| 5) Negative control 2 | S | S |
| 6) Positive control 1 | NS | NS |
| 7) Positive control 2 | NS | NS |

Sterility Test Results:
S = sterile,
NS = non-sterile with positive growth of the test organism All test samples (1-5) were sterile in 24 hours or less with the exception of the positive controls (6-7).

EXAMPLE 12—SIZE OF INSERT VS. BAG VOLUME 0.3 MG/L

The following bags were heated for 60 minutes at 70° C. where the insert was irradiated at 35 kGy-70 KGy.

| Bag Size | Bag Volume (mL) | 35kGy mg of insert | mg insert at 70kGy |
|----------|-----------------|--------------------|--------------------|
| 4" × 6" | 200 | 20 | 5 |
| 6" × 9" | 700 | 70 | 17.5 |
| 7" × 12" | 1600 | 160 | 40 |

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

What is claimed is:

1. A container of a selected volume on the inside suitable for low heat sterilizing a selected article positioned in the inside of the container comprising: a container insert in the selected volume on the inside of the container comprising a melt blown fiber of a diameter 0.5 mm or less of polyoxymethylene or co-polymer of polyoxymethylene having a melt flow rate of between about 20-1200 g/10 minutes at 230° C. as determined by ASTM D1238E that has been irradiated with gamma ionizing irradiation from about 1 to about 200 kGy wherein the polymer is of sufficient quantity to produce a concentration of formaldehyde sufficient for complete sterilization of the article in the container.

2. The container according to claim 1 wherein the fiber diameter is about 0.1 mm or less.

3. The container according to claim 2 wherein the fiber is formed into a non-woven mat.

4. The container according to claim 1 wherein the polyoxymethylene polymer contains ethylene oxide copolymerized to a suitable level for melt blowing into fibers.

5. The container according to claim 1 wherein the melt flow rate is between about 40-1200 g/10 minutes at 230° C.

6. The container according to claim 1 wherein the fiber is part of or attached to the inside of the container.

7. The container according to claim 1 wherein the fiber is heated in an atmosphere of about 5 to 100 percent relative humidity.

8. The container according to claim 1 wherein the fiber is one component of a multi component insert.

9. The container according to claim 1 wherein the fiber further comprises a thermochromic material.

10. The container according to claim 1 wherein the fiber is of sufficient weight and surface area that upon low heating of the insert, the insert releases enough formaldehyde to reach a concentration of at least about 0.1 mg/L in the selected volume.

11. The container according to claim 1 wherein the container is an essentially flat container having a selected length and width.

12. The container according to claim 11 wherein the fiber is formed into a non-woven mat having a mat length and width and wherein the mat length and width is selected such that the mat fits in the container and is of a size of at least about half the product of the length times the container width.

13. The container according to claim 1 wherein the melt flow rate is from about 20 to 500 g/10 minutes at 230° C.

* * * * *